United States Patent
Kalidindi et al.

(10) Patent No.: US 9,572,995 B2
(45) Date of Patent: Feb. 21, 2017

(54) CREATING AND USING A VIRTUAL VIDEO ASSET IN A VIDEO PROVISIONING SYSTEM

(75) Inventors: Srirama Kalidindi, Flower Mound, TX (US); Sanjay Ahuja, Irving, TX (US); John Trimper, Groton, MA (US); Laxmi A. Arte, Austin, TX (US)

(73) Assignee: VERIZON PATENT AND LICENSING INC., Basking Ridge, NJ (US)

( * ) Notice: Subject to any disclaimer, the term of this patent is extended or adjusted under 35 U.S.C. 154(b) by 1083 days.

(21) Appl. No.: 13/196,803

(22) Filed: Aug. 2, 2011

(65) Prior Publication Data
US 2012/0079537 A1    Mar. 29, 2012

Related U.S. Application Data

(60) Provisional application No. 61/387,939, filed on Sep. 29, 2010.

(51) Int. Cl.
| | |
|---|---|
| G06Q 99/00 | (2006.01) |
| A61N 5/06 | (2006.01) |
| H04N 21/2225 | (2011.01) |
| H04N 21/258 | (2011.01) |
| H04N 21/2668 | (2011.01) |
| H04N 21/431 | (2011.01) |

(Continued)

(52) U.S. Cl.
CPC ........ A61N 5/0618 (2013.01); H04N 21/2225 (2013.01); H04N 21/25891 (2013.01); H04N 21/2668 (2013.01); H04N 21/4316 (2013.01); H04N 21/4755 (2013.01); H04N 21/47202 (2013.01); H04N 21/84 (2013.01); H04N 21/8549 (2013.01); G06Q 20/123 (2013.01); G06Q 20/1235 (2013.01); H04N 21/472 (2013.01); H04N 21/482 (2013.01)

(58) Field of Classification Search
CPC .................... G06Q 20/123; G06Q 20/1235; H04N 21/472; H04N 21/482
USPC ..................................... 705/27.1
See application file for complete search history.

(56) References Cited

U.S. PATENT DOCUMENTS 5,892,900 A * 4/1999 Ginter ............... G06F 21/10
  726/26
8,037,506 B2 * 10/2011 Cooper et al. ............ 725/93
(Continued)

OTHER PUBLICATIONS http://www.amazon.com/Lincoln-Lawyer-Marisa-Tomei/dp/B004EPYZP8/ref=sr_1_1?2=dv, 7 pages, print date: Jun. 9, 2011.
(Continued)

*Primary Examiner* — James D Nigh

(57) ABSTRACT

A system may receive, from a content provider, metadata associated with a video asset, where the metadata includes information associated with the video asset and identifies a future time when the video asset will be available for distribution. The system may further process the metadata to create a virtual asset associated with the video asset, where the processed metadata include at least an indication that the metadata is associated with the virtual asset; publish the virtual asset to a store front that allows the user device to select the virtual asset to obtain the virtual asset; and transmit a notification or the video asset, to the user device and at the future time, based on the selection of the virtual asset by the user device, where the notification indicates that the video asset is available to be downloaded.

24 Claims, 7 Drawing Sheets

(51) Int. Cl.
*H04N 21/475* (2011.01)
*H04N 21/84* (2011.01)
*H04N 21/8549* (2011.01)
H04N 21/472 (2011.01)
G06Q 20/12 (2012.01)
H04N 21/482 (2011.01)

(56) References Cited

U.S. PATENT DOCUMENTS

| | | | |
|---|---|---|---|
| 8,122,472 B2* | 2/2012 | Krieger et al. | 725/53 |
| 2007/0220575 A1* | 9/2007 | Cooper | H04N 7/1675 |
| | | | 725/118 |
| 2008/0276278 A1* | 11/2008 | Krieger | H04N 5/44543 |
| | | | 725/40 |
| 2013/0005471 A1* | 1/2013 | Chung | A63F 13/12 |
| | | | 463/42 |

OTHER PUBLICATIONS http://www.amazon.com/s/ref=nb_sb_ss_c_3_14url=search-alias%3Ddvd&field keywords, 4 pages, print date: Jun. 9, 2011.

* cited by examiner

| ASSET ID 405 | TITLE 410 | GENRE 415 |
|---|---|---|
| DESCRIPTION 420 | CAST INFO 425 | RATING 430 |
| PRICE 435 | AVAILABILITY / STATUS 440 | CATEGORY 445 |
| REVIEWS 450 | COVER ART 455 | BUNDLE 460 |

CREATING AND USING A VIRTUAL VIDEO ASSET IN A VIDEO PROVISIONING SYSTEM

REFERENCE TO RELATED APPLICATION

This application claims priority to U.S. Provisional Patent Application No. 61/387,939, filed Sep. 29, 2010, the entire contents of the provisional application being incorporated herein by reference.

BACKGROUND

Users, of user devices, have a growing array of sources, networks, and/or content providers from which to obtain video content and/or services. The users may use video client devices (e.g., a set top box, etc.) to obtain free broadcast television video content (e.g., from Fox, ABC, CBS, etc.), on-demand video content (e.g., Video On-Demand (VOD), pay-per-view (PPV), etc.), and/or pay television video content (e.g., from HBO, Cinemax, etc.) from cable television operators (e.g., Comcast, Time Warner, etc.) and/or satellite television operators (e.g., DirectTV, Dish Network, etc.). The users may use computer devices, wireless mobile handset devices, etc. to obtain other video content from on-line content providers, such as television operators (e.g., ABC, Fox, CBS, etc.), over-the-top (OTT) content providers (e.g., Hulu, Veoh, Jaman, YouTube, etc.), and/or other commercial content providers (e.g., Apple Computer's iTunes, Netflix, Blockbuster, etc.).

BRIEF DESCRIPTION OF THE DRAWINGS

FIG. 4 is a diagram of an example data structure that stores metadata associated with a video asset and/or a virtual video asset according to an implementation described herein;

DETAILED DESCRIPTION OF PREFERRED EMBODIMENTS

The following detailed description refers to the accompanying drawings. The same reference numbers in different drawings may identify the same or similar elements.

Systems and/or methods, described herein, may enable a virtual video asset (hereinafter referred to as a "virtual asset") to be created, managed, stored, and/or provisioned by a video provisioning system (VPS). The term virtual asset, as described herein, may include metadata associated with a video asset that is not currently stored by the VPS. Additionally, or alternatively, a virtual asset may include metadata associated with a video asset that is stored by the VPS, but is not currently available for distribution and/or will be available for distribution at a future point in time. The metadata may describe the video asset and/or may enable the video asset and/or the virtual asset to be processed, managed, offered to the user device, and/or provisioned, by the VPS, to the user device.

The systems and/or methods may enable different types of user devices, such as computer devices (e.g., desktop computers, laptop computers, and tablet computers), wireless handheld devices (e.g., mobile phones, smart phones, personal digital assistants (PDAs), and tablet computers), gaming devices, and/or set top boxes, to access and/or select the virtual asset, via a store front associated with the video provisioning system. The store front may, for example, be an interactive media guide (IMG) (e.g., for set top boxes), a user interface, a webpage, an interactive program guide (IPG), etc. via which the different types of user devices may access, browse, search, and/or select metadata associated with video assets and/or virtual assets.

The systems and/or methods may permit the virtual asset to be sent to a user device, which allows a user, of the user device, to read a description of the virtual asset, view cover art associated with the virtual asset, read reviews associated with the virtual asset, etc. The systems and/or methods may send a notification, to the user device, that indicates that the video asset, to which the virtual asset corresponds, is not yet available and/or identifies a date when the video asset will be available. The systems and/or methods may allow the user device to bookmark the virtual asset, which may cause the VPS to notify the user device when the video asset becomes available for distribution. The systems and/or methods may allow the user device to purchase, rent, or subscribe to the virtual asset prior to the date of availability, which may cause the VPS to automatically transmit the video asset, to the user device, when the video asset becomes available and/or is obtained from a content provider.

Figure 1:
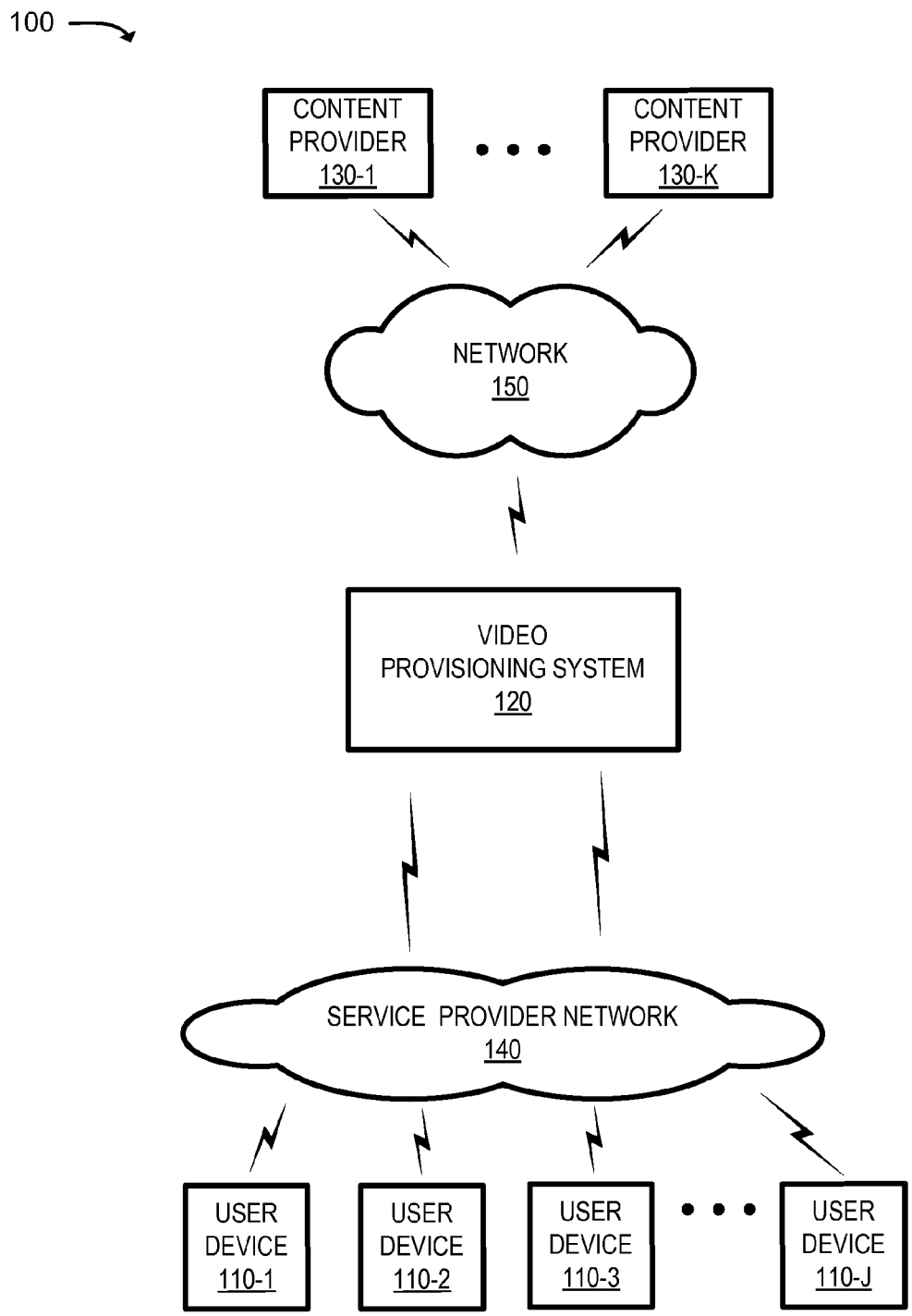
FIG. 1 is a diagram of an example environment in which the systems and/or methods, described herein, may be implemented.

FIG. 1 is a diagram of an example environment in which the systems and/or methods, described herein, may be implemented. As shown in FIG. 1, environment 100 may include a group of user devices 110-1, . . . , 110-J (where J≥1) (hereinafter referred to collectively as "user devices 110" and individually as "user device 110"), a video provisioning system (VPS) 120, a group of content providers 130-1, . . . , 130-K (where K≥1) (hereinafter referred to collectively as "content providers 130" and individually as "content provider 130"), a service provider network 140, and a network 150. The number of devices, systems, and/or networks, illustrated in FIG. 1, is provided for explanatory purposes only. In practice, there may be additional devices, systems, and/or networks; fewer devices, systems, and/or networks; different devices, systems, and/or networks; or differently arranged devices, systems, and/or networks than illustrated in FIG. 1.

Also, in some implementations, one or more of the devices of environment 100 may perform one or more functions described as being performed by another one or more of the devices of environment 100. Devices, systems, and/or networks of environment 100 may interconnect via wired connections, wireless connections, or a combination of wired and wireless connections.

User device 110 may include a computation or communication device that is capable of communicating with service provider network 140. For example, user device 110 may include a radiotelephone, a personal communications system (PCS) terminal (e.g., that may combine a cellular radiotelephone with data processing and data communications capabilities), a personal digital assistant (PDA) (e.g., that can include a radiotelephone, a pager, Internet/intranet access, etc.), a laptop computer, a tablet computer, a set top box, a digital video recorder (DVR), a personal gaming system, a smart phone, or another type of computation or communication device.

User device 110 may communicate with VPS 120 and/or perform certain operations to obtain a video asset from VPS 120. For example, user device 110 may access a store front (e.g., a website, a user interface, an interactive program guide (IPG), an interactive media guide (IMG), etc.) associated with VPS 120, to browse, search, select, and/or obtain a video asset.

VPS 120 may include one or more devices that gather, process, search, store, and/or provide information in a manner similar to that described herein. VPS 120 may be capable of communicating with content providers 130 via network 150 and/or user devices 110 via service provider network 140. VPS 120 may provide a video provisioning service to user devices 110.

VPS 120 may, for example, perform operations associated with video content ingestion, processing, and/or distribution for one or more types of user devices 110, associated with a user, within environment 100. Video content may include, for example, a video asset and/or metadata associated with the video asset. VPS 120 may communicate with one or more content providers 130 to acquire video content. VPS 120 may connect to a collection of different types user devices 110 associated with a user, such as, for example, a set top box, a computer device, a wireless handheld device, and/or other types of user devices 110. VPS 120 may connect to the set top box via a television service provider network 140 (e.g., a cable television network, a satellite television network, a fiber optic television network, or some combination thereof). VPS 120 may connect to the computer device via a broad band service provider network 140 (e.g., via the Internet). VPS 120 may connect to the wireless handset device via a wireless service provider network 140. VPS 120 may perform an ingestion operation on the acquired video content. VPS 120 may process and/or publish the ingested video content in a manner that allows the video asset to be offered and/or distributed to the different types of user devices 110.

Content provider 130 may include any type or form of content provider. For example, content provider 130 may include free television broadcast providers (e.g., local broadcast providers, such as NBC, CBS, ABC, and/or Fox), for-pay television broadcast providers (e.g., TNT, ESPN, HBO, Cinemax, CNN, etc.), and/or Internet-based content providers (e.g., Youtube, Vimeo, Netflix, Hulu, Veoh, etc.) that stream content from web sites and/or permit content to be downloaded (e.g., via progressive download, etc.). Content provider 130 may include on-demand content providers (e.g., video on demand (VOD), pay per view (PPV), etc.). A media stream, as used herein, may refer to a stream of content that includes video content (e.g., a video stream), audio content (e.g., an audio stream), and/or textual content (e.g., a textual stream).

The term video asset, as used herein, may include VOD content, pay-per-view (PPV) video content, rented video content, free television content (e.g., from free television broadcasters, etc.), paid for television content (e.g., from pay television content providers), on-line video content (e.g., on-line television programs, movies, videos, etc.), advertising, games, music videos, promotional information (e.g., such as previews, trailers, etc.), etc. A video asset may be stored in one or more video files that contain video information that can be played on a user device.

Content provider may provide metadata associated with video assets. The metadata may describe the video asset and/or may enable the video asset to be processed, stored, managed, offered, and/or distributed to user device 110. Content provider 130 may, in another example, provide metadata, associated with video assets that are not yet available for distribution to user devices 110. The metadata may identify a date when the video assets can be made available and/or distributed to user devices 110.

Service provider network 140 may include one or more wired and/or wireless networks via which user devices 110 communicate with and/or receive video content from VPS 120. For example, service provider network 140 may include a cellular network, the Public Land Mobile Network (PLMN), a second generation (2G) network, a third generation (3G) network, a fourth generation (4G) network (e.g., a long term evolution (LTE) network), a fifth generation (5G) network, and/or another network. Additionally, or alternatively, service provider network 140 may include a code division multiple access (CDMA) network, a global system for mobile communications (GSM) network, a general packet radio services (GPRS) network, or a combination of CDMA, GSM, and/or GPRS networks. Additionally, or alternatively, service provider network 140 may include a wide area network (WAN), a metropolitan area network (MAN), an ad hoc network, an intranet, a fiber optic-based network (e.g., a fiber optic service (FiOS) network), a television network, and/or a combination of these or other types of networks.

Network 150 may include one or more wired and/or wireless networks. For example, network 150 may include a cellular network, the PLMN, a 2G network, a 3G network, a 4G network (e.g., an LTE network), a 5G network, and/or another network. Additionally, or alternatively, network 150 may include a WAN, a MAN, a telephone network (e.g., the Public Switched Telephone Network (PSTN)), an ad hoc network, an intranet, the Internet, a fiber optic-based network, and/or a combination of these or other types of networks.

Figure 2:
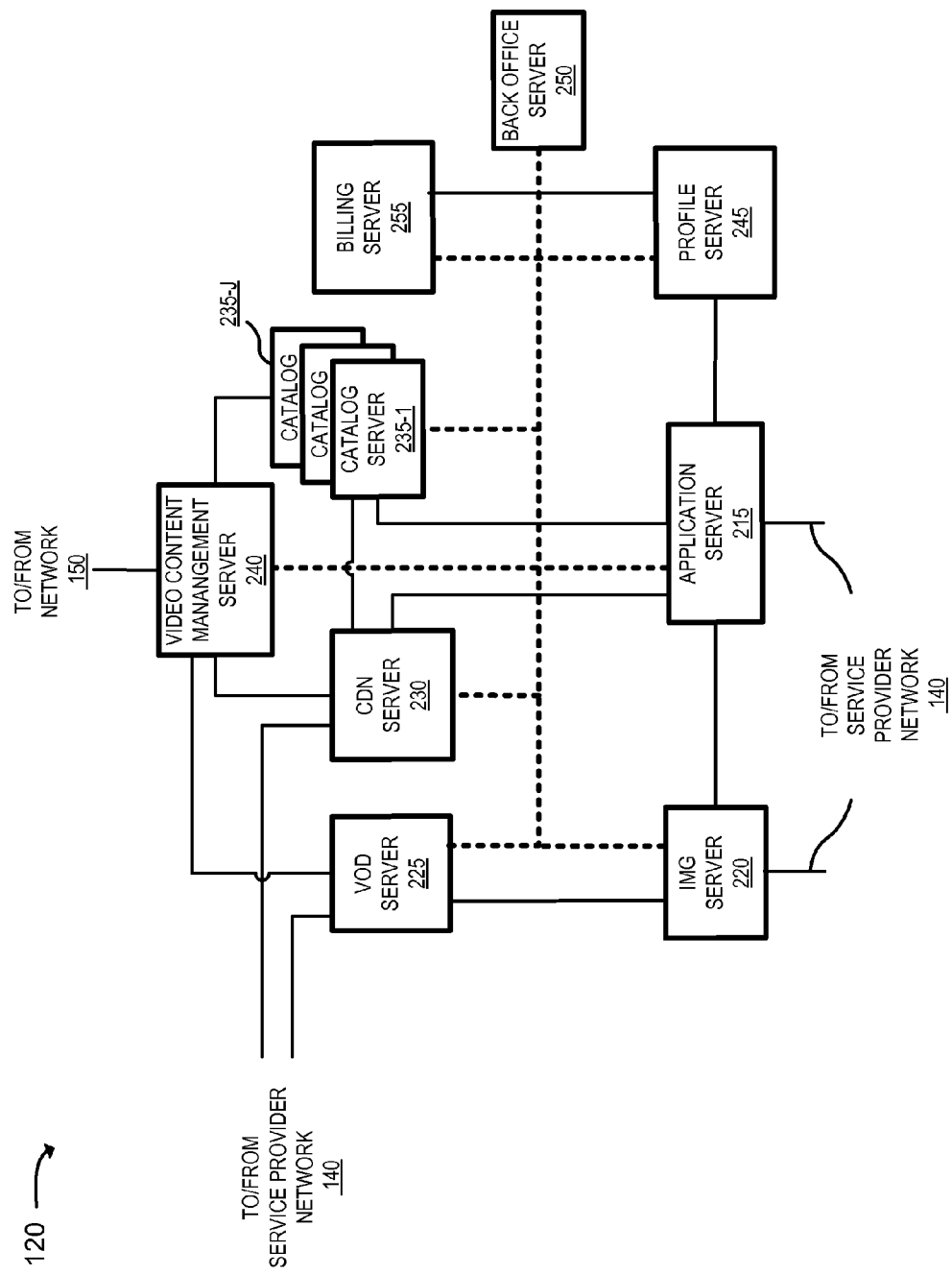
FIG. 2 is a diagram of example devices, associated with the video provisioning system, of FIG. 1.

FIG. 2 is a diagram of example devices associated with VPS 120. VPS 120 may include an application server 215, an interactive media guide (IMG) server 220, a video on-demand (VOD) server 225, a content delivery network (CDN) server 230, a group of catalog servers 235-1, . . . , 235-J (where J≥1) (hereinafter referred to collectively as "catalog servers 235" and individually as a "catalog server 235"), a video content management (VCM) server 240, a profile server 245, a back office server 250 (hereinafter referred to as "BOS 250"), and a billing server 255. Although FIG. 2 shows example devices of VPS 120, in other implementations, VPS 120 may include fewer devices, additional devices, different devices, or differently arranged devices than depicted in FIG. 2. Additionally, or alternatively, one or more devices of VPS 120 may perform one or more tasks described as being performed by one or more other devices of VPS 120.

In the description below, VOD server 225 is described as provisioning video services for a type of user device 110 (i.e., a set top box) and CDN server 230 is described as provisioning video services for another type of user device 110 (i.e., a computer device, a wireless handset device, etc.) for explanatory purposes. In another implementation, the video services may be provisioned for the set top box and/or the other types of user devices 110 in a number of ways. For example, VOD server 225 and/or CDN server 230 may be combined into a single device that provisions the video services for each type of user device 110. In another example, the video services may be provisioned, for each type of user device 110, by another device and/or network instead of, or in combination with, VOD server 225 and/or CDN server 230. Additionally, IMG server 220 is described as providing an a store front (i.e., via an IMG), that can be accessed by the set top box, and application server 215 is described as providing another store front (e.g., via a web page, a user interface, an interactive program guide, etc.), that can be accessed by the other types of user devices 110, for explanatory purposes. In another implementation, the store front may be provisioned for the set top box and/or the other types of user devices 110 in a number of ways. For example, IMG server 220 and/or application server 215 may be combined into a single device that provisions the store front for each type of user device 110. In another example, the store front may be provisioned, for each type of user device 110, by another device and/or network instead of, or in combination with, IMG server 220 and/or application server 215. Thus, the examples below are provided for explanatory purposes only.

Application server 215 may include one or more server devices, or other types of computation or communication devices, that gather, process, search, store, and/or provide information in a manner similar to that described herein. Application server 215 may receive metadata that has been published by catalog server 235. The metadata may, in one example, be associated with video assets that are stored in CDN server 230. The metadata, in another example, may correspond to virtual assets (e.g., video asset that are not yet available and/or that are not yet stored in CDN server 230).

Application server 215 may host a store front (e.g., a VPS store front), such as a private website (e.g., for subscribing user devices 110), a public website (e.g., for non-subscribing user devices 110), a user interface (UI) (e.g., that is accessible by wireless handset user devices 110, etc.), an interactive program guide (e.g., an IMG for set top box-type user devices 110) and/or other types of user interfaces. The store front may enable single sign-on (SSO) store front access, to a user of one or more user devices 110, based on the same login credentials (e.g., username, password, personal identification number (PIN), etc.). Application server 215 may publish all or a portion of the metadata, associated with the video assets and/or virtual assets, to the store front that permits any of user devices 110 to browse, perform searches, process payment, etc. for video assets and/or virtual assets based on the metadata that is published to the store front.

Application server 215 may store information associated with a transaction history that corresponds to a type of user device 110 (e.g., a computer user device 110, a wireless handheld user device 110, a gaming user device 110, etc.) that is different than a set top box user device 110. The transaction history may include information regarding prior transactions (e.g., purchases, rentals, subscriptions, etc.), associated with one or more video assets and/or virtual assets, by user device 110. The transaction history may also identify a period of time during which a rental period or subscription period, for a video asset, is valid. The transaction history may identify when a video asset, to which a virtual asset that has been purchased, rented, or subscribed to corresponds, becomes available and/or is to be distributed to user device 110. Application server 215 may transmit information, associated with the transaction history, to profile server 245, to be stored in a user profile associated with a user of user device 110.

IMG server 220 may include one or more server devices, or other types of computation or communication devices, that gather, process, search, store, and/or provide information in a manner similar to that described herein. IMG server 220 may, for example, process metadata, that has been published by catalog server 235 and/or VOD server 225, in a manner similar to that described above (e.g., with respect to application server 215). The metadata may be associated with video assets that are stored in VOD server 225. The metadata may, in another example, correspond to virtual assets (e.g., video asset that are not yet available and/or that are not yet stored in VOD server 225). The metadata may be accessed and/or obtained, via IMG server 220, by a particular type of user device 110, such as a set top box user device 110.

IMG server 220 may publish all or a portion of the metadata, associated with the video assets and/or virtual assets, to a store front that the set top box user device 110, associated with the user, may render for display on a video display device. IMG server 220 may permit the set top box user device 110 to access information associated with video assets that stored by VOD server 225. IMG server 220 may permit the set top box user device 110 to access virtual assets that correspond to video assets that are not yet stored in VOD server 225.

IMG server 220 may store information associated with a transaction history that corresponds to a set top box user device 110. The transaction history may include information regarding prior transactions (e.g., purchases, rentals, subscriptions, etc.), associated with one or more video assets and/or virtual assets, by set top box user device 110. The transaction history may also identify a period of time during which a rental period or subscription period, for a video asset, is valid. The transaction history may identify when a video asset, to which a virtual asset that has been purchased, rented, or subscribed to corresponds, becomes available and/or is to be distributed to user device 110. IMG server 220 may, in another example, transmit information, associated with the transaction history, to profile server 245, to be stored in a user profile associated with a user of user device 110.

VOD server 225 may include one or more server devices, or other types of computation or communication devices, that gather, process, search, store, and/or provide information in a manner similar to that described herein. VOD server 225 may, for example, perform operations to receive, store, process, and/or distribute video content in a format that is supported by set top box user devices 110.

VOD server 225 may receive published video assets and/or metadata from VCM server 240. VOD server 225 may store the published video assets in a memory associated with VOD server 225. VOD server 225 may publish the metadata, associated with video assets (e.g., that are available for release) and/or virtual assets, to IMG server 220. In another example implementation, VOD server 225 may communicate with content provider 130 to receive video content directly from content provider 130 (e.g., not via VCM server 240).

CDN server 230 may include one or more server devices, or other types of computation or communication devices, that gather, process, search, store, and/or provide information in a manner similar to that described herein. CDN server 230 may, for example, perform operations to receive, store, process, and/or distribute video content in a format that is supported by one or more types of user devices 110 (e.g., a computer device, a wireless mobile device, a gaming device, etc.) other than, or in addition to, a set top box user device 110. CDN server 230 may actually represent a content delivery network that includes multiple routing and/or storage devices.

CDN server 230 may receive published video assets in multiple video formats from VCM server 240. CDN server 230 may store the published video assets in a memory associated with CDN server 230. CDN server 230 may identify a respective storage location and/or URL for each format of each video asset that are stored within the memory and may send information associated with the storage locations and/or the URLs to catalog server 235. CDN server 230 may provide video assets to wireless handset user devices 110 via a wireless service provider network 140. CDN server 230 may provide the video assets to a computer user device 110 via a broadband service provider network 140 (e.g., the Internet). In another example implementation, CDN server 230 may provide the video assets to a set top box user device 110 via a television service provider network 140 and/or via VOD server 225.

Catalog server 235 may include one or more server devices, or other types of computation or communication devices, that gather, process, search, store, and/or provide information in a manner similar to that described herein. Catalog server 235 may, for example, receive, from VCM server 240, published metadata associated with video assets that have been published to VOD server 225 and/or CDN server 230. In another example, catalog server 235 may receive, from VCM server 240 other published metadata associated with virtual assets (e.g., that correspond video assets that are not stored in VOD server 225 and/or CDN server 230 and/or are not yet available to be released to user devices 110). Catalog server 235 may identify, from the metadata, information associated with the availability of the video assets based on dates on which the video assets are released, blacked out, etc. Catalog server 235 may process and/or package the metadata in order to offer, to user devices 110, the video assets to which the metadata corresponds. Catalog server 235 may process and/or package the other metadata to create a virtual asset that can be offered, to user devices 110. The processed metadata associated with the video assets and/or the processed other metadata, that corresponds to the virtual assets may include identifiers (e.g., video asset numbers, titles, etc.), availability dates, prices (e.g., sale prices, rental prices, subscription prices, etc.), cover art (e.g., images, trailers, etc.), descriptions (e.g., a synopsis, a summary, etc. of the video assets), ratings, reviews, genres, casting information (e.g., actors, directors, producers, etc.), etc. Catalog server 235 may, for example, publish the metadata to the store front associated with application server 215. Catalog server 235 may publish the other metadata, as virtual assets, to the store front associated with VPS application 215.

One catalog server 235, such as catalog server 235-1, may store metadata associated with video assets and/or virtual assets that are accessible by wireless handset user devices 110 (e.g., via a wireless service provider network 140). Another catalog server 235, such as catalog server 235-2, may store metadata associated with video assets and/or virtual assets that are accessible by computer user devices 110 (e.g., via a broadband service provider network 140). Yet another catalog server 235, such as catalog server 235-J, may store metadata associated with video assets and/or virtual assets that are accessible by set top box user devices 110 (e.g., via a television service provider 140).

VCM server 240 may include one or more server devices, or other types of computation or communication devices, that gather, process, search, store, and/or provide information in a manner similar to that described herein. VCM server 240 may, for example, communicate with content providers 130 to ingest video assets to be processed by VPS 120. VCM server 240 may process the video assets to generate copies of the video assets in one or more formats that are supported (e.g., that can be received, processed, and/or played) by the different types of user devices 110. VCM server 240 may publish the one or more formats, associated with the processed video assets, to VOD server 225 and/or CDN server 230.

VCM server 240 may also ingest, process, and/or publish metadata associated with the video assets and/or virtual assets. VCM server 240 may process the metadata to ensure that the metadata is supported by the different types of user devices 210. VCM server 240 may publish the processed metadata to catalog server 235 and/or VOD server 225.

Profile server 245 may include one or more server devices, or other types of computation or communication devices, that gather, process, search, store, and/or provide information in a manner similar to that described herein. Profile server 245 may, for example, store information associated with a profile that includes information regarding the user and/or each user device 110 that the user has registered with VPS 120. For example, information associated with the profile may further include information associated with the user (e.g., a username, password, PIN, etc.), information associated with each user device 110, such as a respective identifier (e.g., a mobile directory number (MDN), an Internet protocol (IP) address, a media access control (MAC) address, a compression/decompression (CODEC) identifier, etc.), and/or information associated with a type of user device 110, such as a computer device (e.g., a lap top computer, a tablet computer, etc.), a wireless mobile device (e.g., a Droid®, a Blackberry®, an iPhone®, etc.), a set top box, a gaming device, etc.

The information associated with the profile may also include a respective transaction history (e.g., prior purchases, prior URLs accessed, prior downloads, etc.) associated with each user device 110; information associated with services for which user device 110 has subscribed; information associated with a location (e.g., an address, a zip code, a city, etc.) of the user and/or user device 110; information associated user account limits, restrictions, etc.; information associated with a language spoken by the user; etc. Profile server 245 may communicate with application server 215 to obtain a first transaction history, associated with user device 110, that are different types of user devices 110 than a set top box user device 110, such as a computer user device 110, a wireless handheld user device 110, a gaming user device 110, etc. Profile server 245 may communicate with IMG server 220 to obtain a second transaction history, associated with a set top box user device 110. Profile server 245 may store information obtained from the first transaction history and/or the second transaction history in a user profile associated with a user of the set top box user device 110 and/or user device 110.

The information associated with the profile may include a bookmark that identifies metadata associated with a video asset and/or virtual asset that that have been selected by a user of user device 110. The bookmark may cause metadata, associated with a bookmarked video asset and/or virtual asset, to be stored in the user profile that enables the user to access the metadata within a period of time that is less than another period of time associated with obtaining the metadata (e.g., based on browsing, searching, etc.) via the store front (e.g., application server 215 and/or IMG server 220).

BOS 250 may include one or more server devices, or other types of computation or communication devices, that gather, process, search, store, and/or provide information in a manner similar to that described herein. BOS 250 may communicate with VCM server 240 to ensure that metadata, associated with a virtual asset, is processed and/or published to VOD server 225 and/or catalog server 235. BOS 250 may communicate with IMG server 220 and/or application server 215 to process requests for virtual assets. For example, BOS 250 may receive a request for a virtual asset from user device 110, via application server 215 and/or IMG server 220. BOS 250 may, in response to the request, communicate with profile server 245 to obtain a user profile associated with the user of user device 110. BOS 250 may identify a type of user device 110 based on information associated with the user profile. BOS 250 may retrieve metadata, associated with the virtual asset, that corresponds to the type of user device 110 identified by the user profile. BOS 250 may obtain, from the metadata, a date when a video asset, to which the virtual asset corresponds, is expected to be available. BOS 250 may transmit the metadata to the user device 110, via application server 215. BOS 250 may generate a notification that identifies the date when the video asset, to which the virtual asset corresponds, is expected to be available for distribution to user device 110. BOS 250 may transmit the notification to user device 110 via application server 215.

BOS 250 may receive, from user device 110, a request to bookmark the virtual asset. BOS 250 may cause metadata, associated with the virtual asset, to be stored, as a bookmark, in the user profile. Storing the metadata, associated with the virtual asset, in the user profile may permit the user, of user device 110, to access the virtual asset within a period of time that is less than another period of time associated with accessing the virtual asset via the store front. BOS 250 may store a list of user devices 110 that have bookmarked the video asset.

BOS 250 may receive, from user device 110, a request to purchase, rent, and/or subscribe to a video asset, associated with a virtual asset, prior to the video asset becoming available and/or being published to VOD server 225 and/or CDN server 230. BOS 250 may communicate with billing server 255 to perform an electronic transaction associated with the virtual asset. BOS 205 may transmit information, regarding the electronic transaction associated with the virtual asset, to application server 215, IMG server 220, and/or profile server 245 to be stored in a transaction history associated with the user of user device 110. BOS 250 may store a list of user devices 110 that have bookmarked the video asset.

BOS 250 may receive an indication, from VCM server 240, that indicates that a video asset, to which the virtual asset corresponds, has been ingested, processed and/or published to VOD server 225 and/or CDN server 235. BOS 250 may transmit a notification to user devices 110 that have bookmarked the virtual asset (e.g., based on the list of user devices 110 that bookmarked the virtual asset) and/or purchased, rented and/or subscribed to the virtual asset (e.g., based on the list of user devices 110 that purchases, rented, and/or subscribed to the virtual asset). The notification may indicate that the video asset, to which the virtual asset corresponds, is available to be downloaded.

BOS 250 may, in another example, instruct VOD server 225 to automatically distribute the video asset to set top box user devices 110 that are included in the list of user devices 110 that purchased, rented, and/or subscribed to the virtual asset. BOS 250 may, in yet another example, instruct CDN server 230 to automatically distribute the video asset to other types of user devices 110 (e.g., computer devices, wireless handheld device, etc.) that are included in the list of user devices 110 that purchased, rented, and/or subscribed to the virtual asset.

Billing server 255 may include one or more server devices, or other types of computation or communication devices, that gather, process, search, store, and/or provide information in a manner similar to that described herein. Billing server 255 may, for example, perform billing operations associated with accounts that correspond to each user device 110 associated with a user. Billing server 255 may perform electronic transactions associated with a purchase, rent, subscription, etc. of a video asset and/or virtual asset. When performing the electronic transaction, billing server 255 may process payment information associated with the electronic transaction.

Figure 3:
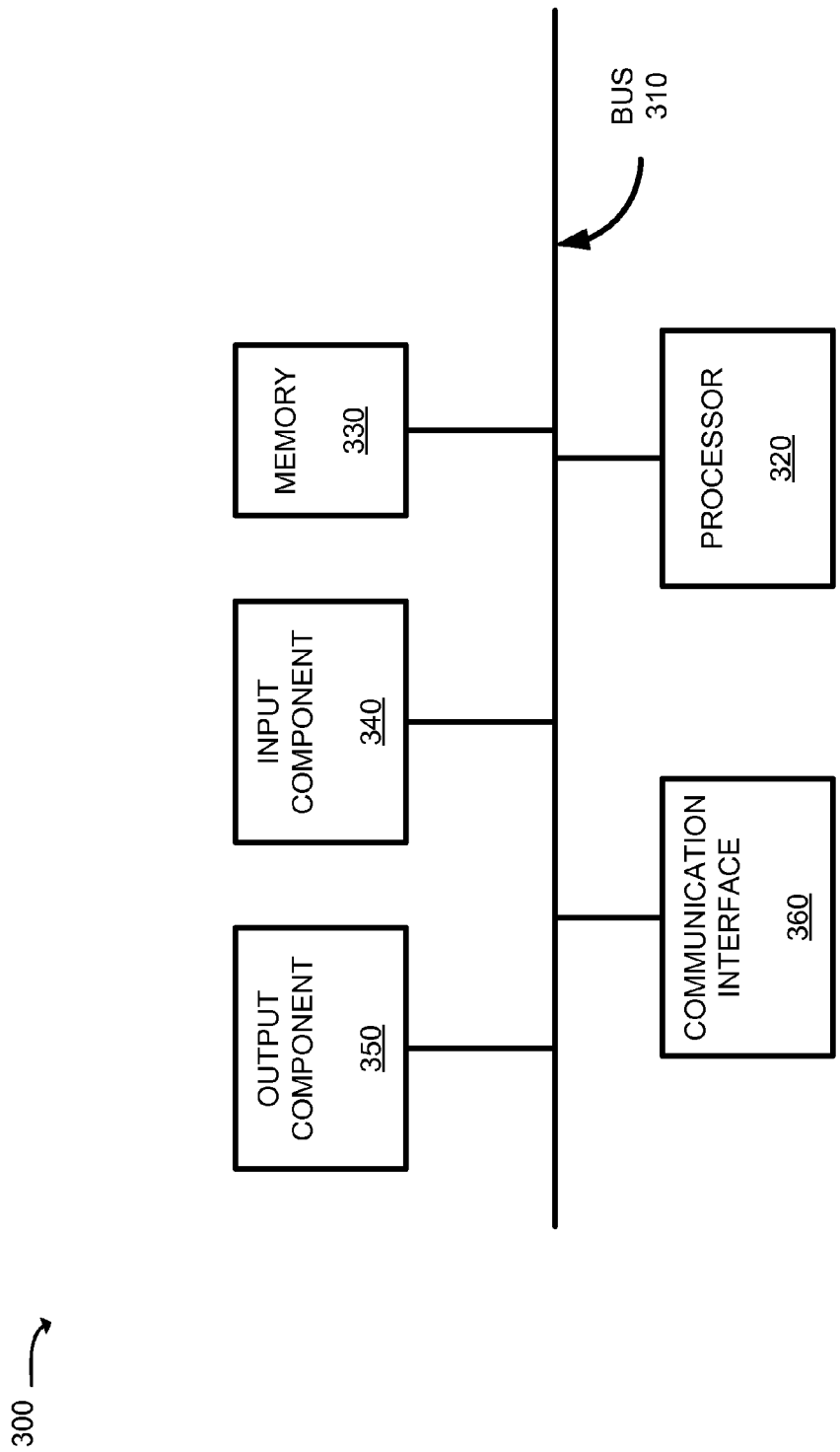
FIG. 3 is a diagram of example components that correspond to one or more of the devices of FIGS. 2 and/or 3.

FIG. 3 is a diagram of example components of a device 300 that may correspond to user device 110, content provider 130, application server 215, IMG server 220, VOD server 225, CDN server 230, catalog server 235, VCM server 240, profile server 245, BOS 250, and/or billing server 255. Alternatively, each of user device 110, content provider 130, application server 215, IMG server 220, VOD server 225, CDN server 230, catalog server 235, VCM server 240, profile server 245, BOS 250, and/or billing server 255 may include one or more devices 300. Device 300 may include a bus 310, a processor 320, a memory 330, an input component 340, an output component 350, and a communication interface 360. Although FIG. 3 shows example components of device 300, in other implementations, device 300 may contain fewer components, additional components, different components, or differently arranged components than depicted in FIG. 3. For example, device 300 may include one or more switch fabrics instead of, or in addition to, bus 310. Additionally, or alternatively, one or more components of device 300 may perform one or more tasks described as being performed by one or more other components of device 300.

Bus 310 may include a path that permits communication among the components of device 300. Processor 320 may include a processor, microprocessor, or processing logic that may interpret and execute instructions. Memory 330 may include any type of dynamic storage device that may store information and instructions, for execution by processor 320, and/or any type of non-volatile storage device that may store information for use by processor 320.

Input component 340 may include a mechanism that permits a user to input information to device 300, such as a keyboard, a keypad, a button, a switch, etc. Output component 350 may include a mechanism that outputs information to the user, such as a display, a speaker, one or more light emitting diodes (LEDs), etc. Communication interface 360 may include any transceiver-like mechanism that enables device 300 to communicate with other devices and/or systems via wireless communications (e.g., radio frequency, infrared, and/or visual optics, etc.), wired communications (e.g., conductive wire, twisted pair cable, coaxial cable, transmission line, fiber optic cable, and/or waveguide, etc.), or a combination of wireless and wired communications. For example, communication interface 360 may include mechanisms for communicating with another device or system via a network, such as service provider network 140 and/or network 150. In one alternative implementation, communication interface 360 may be a logical component that includes input and output ports, input and output systems, and/or other input and output components that facilitate the transmission of data to other devices.

As will be described in detail below, device 300 may perform certain operations relating virtual assets within a video provisioning system. Device 300 may perform these operations in response to processor 320 executing software instructions contained in a computer-readable medium, such as memory 330. A computer-readable medium may be defined as a non-transitory memory device. A memory device may include space within a single physical memory device or spread across multiple physical memory devices. The software instructions may be read into memory 330 from another computer-readable medium or from another device. The software instructions contained in memory 330 may cause processor 320 to perform processes described herein. Alternatively, hardwired circuitry may be used in place of or in combination with software instructions to implement processes described herein. Thus, implementations described herein are not limited to any specific combination of hardware circuitry and software.

FIG. 4 is a diagram of an example data structure 400 that stores metadata associated with a video asset and/or a virtual asset according to an implementation described herein. Catalog server 235 may store the metadata, published by VCM server 240, in data structure 400. Data structure 400 may include a collection of fields, such as an asset identifier (ID) field 405, a title field 410, a genre field 415, a description field 420, a cast information (info) field 425, a rating field 430, a price field 435, an availability/status field 440, a category field 445, a reviews field 450, a cover art field 455, and a bundle field 460. Data structure 400 includes fields 405-460 for explanatory purposes. In practice, data structure 400 may include additional fields, fewer fields, different fields, or differently arranged fields than are described with respect to data structure 400.

Asset ID field 405 may store a unique identifier (e.g., one or more sequences of characters, etc.) associated with a particular video asset and/or virtual asset. In one example, the unique identifier may include an indication (e.g., one or more characters of the sequences of characters) that distinguishes a video asset from a virtual asset. Title field 410 may store a title associated with the particular video asset and/or virtual asset. In one example, the title may include an indication (e.g., such as an asterisk, a symbol, or some other indication) that indicates, to a user, of user device 110, that the title is associated with a virtual asset. Genre field 415 may store information associated with a genre that corresponds to the particular video asset and/or virtual asset. Description field 420 may store a description associated with the particular video asset and/or virtual asset, such as a summary of a movie, a television program, etc. In one example, the description may include an indication that the description is associated with a virtual asset. The indication may, in another example, include information that identifies when the video asset, to which the virtual asset corresponds, will be available to be downloaded by user device 110. Cast info field 425 may store information associated with an actor, a director, a producer, and/or other individuals associated with the particular video asset and/or virtual asset.

Rating field 430 may store information associated with a rating (e.g., general audience (G), parental guidance (PG), PG-13, restricted (R), mature audience (MA), etc.) that corresponds to the particular video asset and/or virtual asset. Price field 435 may store information, associated with one or more prices, that corresponds to the particular video asset and/or virtual asset. For example, one price may correspond to a sale price for the particular video asset. Another price may correspond to a rental price (e.g., a cost per viewing, per day, per week, etc.). One or more further prices may correspond to a price associated with a bundle of video assets, virtual assets, and/or services that include the particular video asset and/or virtual asset. In another example, price field 435 may store prices that are expected to correspond with a video asset, with which the virtual asset is associated, when the video asset is received from content provider 130, is stored in VOD server 225 and/or CDN server 230, and/or is available to be distributed to user devices 110.

Availability/status field 440 may store information associated with an availability of the particular video asset and/or virtual asset. For example, availability/status field 440 may store information that identifies when the particular video asset may be released to users of user devices 110 and when the particular asset is no longer available to users of user devices 110. In another example, availability/status field 440 may store information associated with a blackout period from a time when the particular asset is not to be released to another time when the particular asset may be released. In yet another example, availability/status field 440 may store information that indicates whether the unique identifier, identified in asset ID field 405, corresponds to a video asset and/or a virtual asset. Availability/status field 440 may store information that identifies when a video asset, to which the particular virtual asset corresponds, will be received from content provider 130, stored in VOD server 225 and/or CDN server 230, and/or made available for distribution to user devices 110.

Category field 445 may store information associated with a category that corresponds to the particular video asset and/or virtual asset. The information, associated with the category, may include, for example, an indication that the particular video asset and/or virtual asset corresponds to a movie, a television program, a video game, etc. Reviews field 450 may include information associated with reviews, by users associated with VPS 220 and possibly users not associated with VPS 220, of the particular video asset and/or virtual asset. In one example, the information associated with the reviews may correspond to reviews of a video asset with which the particular virtual asset corresponds. The reviews may be reviews of the video asset prior to the video asset being released to the public, ingested by VCM server 240, stored in VOD server 225 and/or CDN server 230, and/or made available for distribution to user devices 110.

Cover art field 455 may include one or more images associated with the particular asset and/or virtual asset. The one or more images may be associated with a scene, branding, a cast member, etc. associated with the virtual asset and/or video asset. Bundle field 460 may store information, associated with a bundle, that identifies other services, virtual assets, and/or video assets that are associated with the particular video asset and/or virtual asset. For example, bundle field 460 may store information associated with a package that is being offered, to user devices 110, at a discounted price. The package may include, for example, the particular video asset and/or virtual asset; promotional material associated with the package and/or other packages; and/or another video asset, virtual asset, and/or service. The bundle may be associated with a price identified in price field 435.

Figure 5:
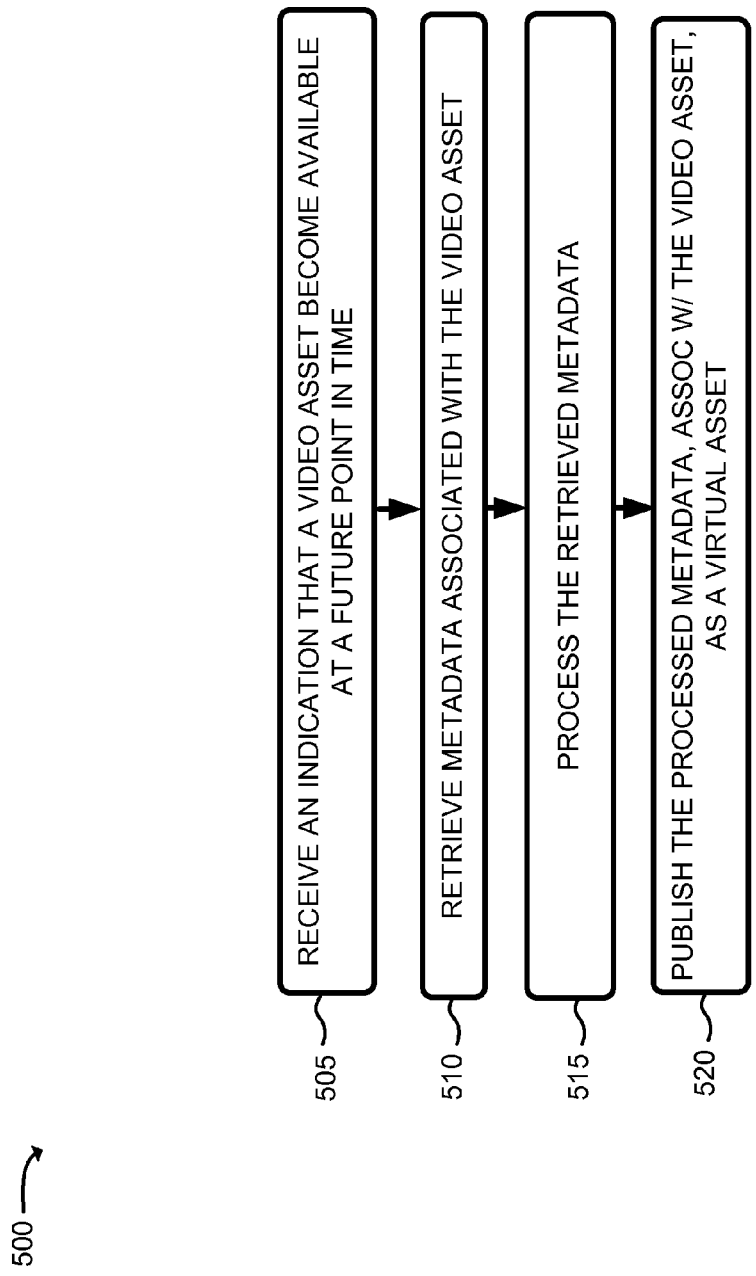
FIG. 5 is a flow chart of an example process for creating a virtual video asset within the video provisioning system.

FIG. 5 is a flow chart of an example process 500 for creating a virtual video asset within video provisioning system 120. In one example implementation, process 500 may be performed by BOS 250. In another example implementation, some or all of process 500 may be performed by a device, or collection of devices separate from, or in combination with BOS 250.

As shown in FIG. 5, process 500 may include receiving an indication that a video asset is to become available at a future point in time (block 505) and retrieving metadata associated with the video asset (block 510). For example, BOS 250 may receive information, associated with a video asset, that indicates that the video asset may be available, at a future point in time, for distribution to user devices 110. The information associated with the video asset may, for example, be received from content provider 130 as an invitation to obtain metadata, associated with the video asset, prior to the future point in time. In another example, BOS 250 may received, via the Internet (e.g., from a web server via network 150), an indication that the video asset can be obtained (e.g., for distribution to user devices 110) at a future point in time. In this example, the indication may be a press release from a movie studio, a news story, a blog posting, etc. that promotes the video asset prior to the future point in time when the video asset becomes available.

BOS 250 may, as a result of receiving the indication, communicate with content provider 130 to obtain the metadata associated with the video asset. The metadata may include all or a portion of the information stored in data structure 400 (FIG. 4). Content provider 130 may, as a result of the communication, transmit the metadata to VCM server 240 to be ingested into VPS 120. In another example, content provider 130 may automatically transmit, to VCM server 240, the metadata associated with the video asset in addition to, or instead of, sending the indication that the video asset may be available at the future point in time.

As also shown in FIG. 5, process 500 may include processing the retrieved metadata (block 515) and publishing the processed metadata, associated with the video asset, as a virtual asset (block 520). For example, VCM server 240 may receive the metadata and may ingest the metadata in a manner similar to that described above in FIG. 2. VCM server 240 may process the metadata to ensure that the metadata is supported by the different types of user devices 210 (e.g., the set top box user device 110, computer user device 110, wireless handheld user device 110, etc.).

BOS 250 may send an indication, to VCM server 240, catalog server 235, and/or VOD server 225, that the processed metadata is to be published as a virtual asset. As a result of the indication, VCM server 240 may store, within the metadata, a unique identifier, associated with the video asset, that indicates that the metadata corresponds to a virtual asset. VCM server 240 may modify a title associated with the video asset that includes an indication that the video asset is a virtual asset. VCM server 240 may store, within a description associated with the video asset, an indication that the video asset is not available to be downloaded and/or that identifies when the video asset may be available to be downloaded by user device 110. VCM server 240 may store, in the metadata, an indication when the video asset will become available and/or a status that indicates that the video asset is associated with the virtual asset. VCM server 240 may publish the processed metadata to catalog server 235 and/or VOD server 225.

Catalog server 235 may receive the metadata and may store the metadata, in a memory associated with catalog server 235, as a virtual asset. Catalog server 235 may publish the metadata, as a virtual asset, to application server 215 to be included in a store front (e.g., a website, a user interface, an IPG, etc.) associated with VPS 120. Storing the virtual asset in the store front may allow computer user devices 110, wireless handheld user devices 110, etc. to access the virtual asset, to bookmark the virtual asset, or to request that the virtual asset be downloaded at a future point in time when the video asset, to which the virtual asset corresponds, becomes available.

In another example, VOD server 225 may receive the metadata and may store the metadata, in a memory associated with VOD server 225, as a virtual asset. VOD server 225 may publish the metadata, as a virtual asset, to IMG server 220 to be included in another store front (e.g., an IMG) associated with VPS 120. Storing the virtual asset in the other store front may allow set top box user devices 110 to access the virtual asset, to bookmark the virtual asset, or to request that the virtual asset be downloaded at the future point in time.

In another example implementation, BOS 250, catalog server 235, and/or VOD server 225 may modify all or a portion of the metadata, in the manner described above, instead of or in addition to VCM server 240.

Figure 6:
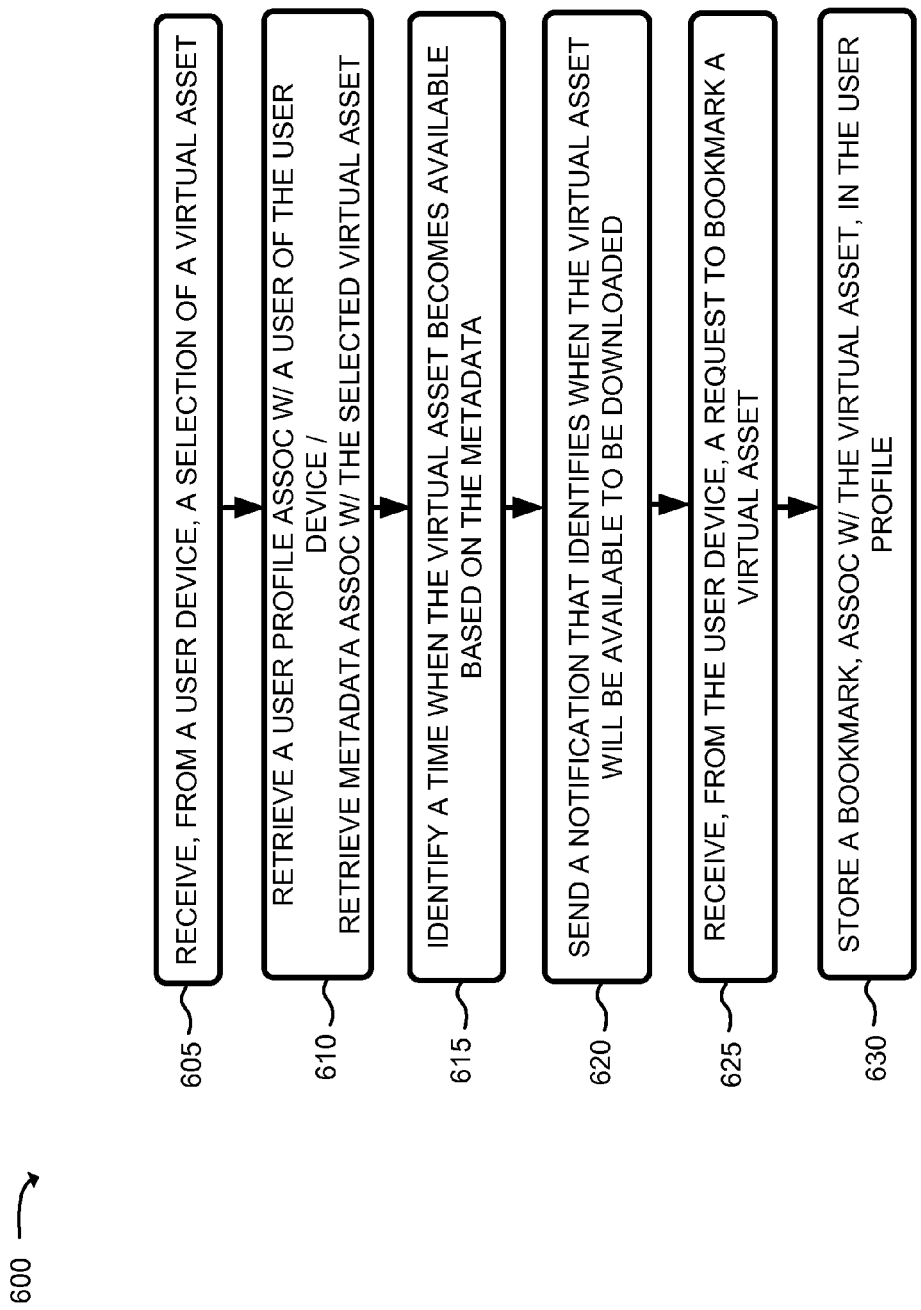
FIG. 6 is a flow chart of an example process for provisioning a virtual asset according to an implementation described herein.

FIG. 6 is a flow chart of an example process 600 for provisioning a virtual asset according to an implementation described herein. In an example implementation, process 600 may be performed by BOS 250. In another example implementation, some or all of process 600 may be performed by a device, or collection of devices separate from, or in combination with BOS 250.

As shown in FIG. 6, process 600 may include receiving, from a user device, a selection of a virtual asset (block 605), and retrieving a user profile associated with a user of the user device and/or metadata associated with the selected virtual asset (block 610). For example, user device 110 may select metadata, associated with a virtual asset, via a store front associated with VPS 120. The metadata, in one example, may represent a title, an image, etc., associated with a video asset to which the virtual asset corresponds. User device 110 may, in one example, be a set top box user device 110 that selects the metadata via an IMG associated with IMG server 220. IMG server 220 may receive the selection of the metadata and may transmit the selection of the metadata to BOS 250. In another example, user device 110 may be a different type of user device 110 (e.g., a computer user device 110, a wireless handheld user device 110, a gaming user device 110, etc.), than the set top box user device 110, that selects the metadata via a website, a user interface, a IPG, etc. associated with application server 215. Application server 215 may receive the selection of the metadata and may transmit the selection of the metadata to BOS 250.

BOS 250 may receive the selection of the metadata and may communicate with catalog server 235 (e.g., when selection of the metadata is received via application server 215) and/or VOD server 230 (e.g., when selection of the metadata is received via IMG server 220) to retrieve all or a portion of the metadata associated with the virtual asset. BOS 250 may also communicate with profile server 245 to retrieve a user profile associated with a user of user device 110. The user profile may include information associated with a type of user device 110 from which the selection was received. The user profile may also include information associated with another user device 110 associated with the user.

As also shown in FIG. 6, process 600 may include identifying a time when the virtual asset becomes available based on the metadata (block 615) and sending a notification that identifies when the virtual asset will be available to be downloaded (block 620). For example, BOS 250 may identify a time when the video asset, to which the virtual asset corresponds, becomes available for distribution to user device 110. The time may, in another example, correspond to when VCM server 240 receives, ingests, and/or processes the video asset. The time may, in yet another example, correspond to when the video asset is stored in VOD server 225 and/or CDN server 230. BOS 250 may transmit a notification to user device 110 (e.g., via application server 215 and/or IMG server 220) that identifies the time when the video asset will be available to be downloaded. The notification may include the metadata associated with the virtual asset.

As further shown in FIG. 6, process 600 may include receiving, from the user device, a request to bookmark the virtual asset (block 625) and storing a bookmark, associated with the virtual asset, in the user profile (block 630). For example, user device 110 may receive the metadata associated with the virtual asset that allows the user, of user device 110, to view the metadata (e.g., a description of the video asset, one or more images associated with the video asset, reviews of the video asset, an expected price associated with the video asset, etc.). User device 110 may send, to BOS 250 and via one of the store fronts (e.g., via application server 215 and/or IMG server 220), a request to bookmark the virtual asset. BOS 250 may receive the request to bookmark the virtual asset and may transmit, to profile server 245, all or a portion of the metadata to be stored the user profile associated with the user. Storing all or the portion of the metadata, in the user profile, may enable user device 110 to access the metadata within a first period of time that is less than a second period of time associated with browsing and/or searching for the video asset via the store front. Additionally, or alternatively, storing all or the portion of the metadata, in the user profile, may enable another user device 110, identified in the user profile, to access the metadata within a third period of time that is less than the second period of time.

BOS 250 may store information associated with user device 110 and/or the other user device 110 in a list, associated with the virtual asset, that identifies each user device 110 that has bookmarked the virtual asset. The list, associated with the virtual asset, may enable BOS 250 to transmit a notification, to each user device 110 identified on the list, that indicates that the video asset is available to be downloaded. For example, BOS 250 may receive, at a later point in time relative to a current time, an indication, from VCM server 240, that the video asset, to which the virtual asset corresponds, has been received and/or processed, and/or is published to VOD server 225 and/or CDN server 230. BOS 250 may, in response to the indication, send a notification to each of the user devices, indicating that the video asset is available to be downloaded.

Figure 7:
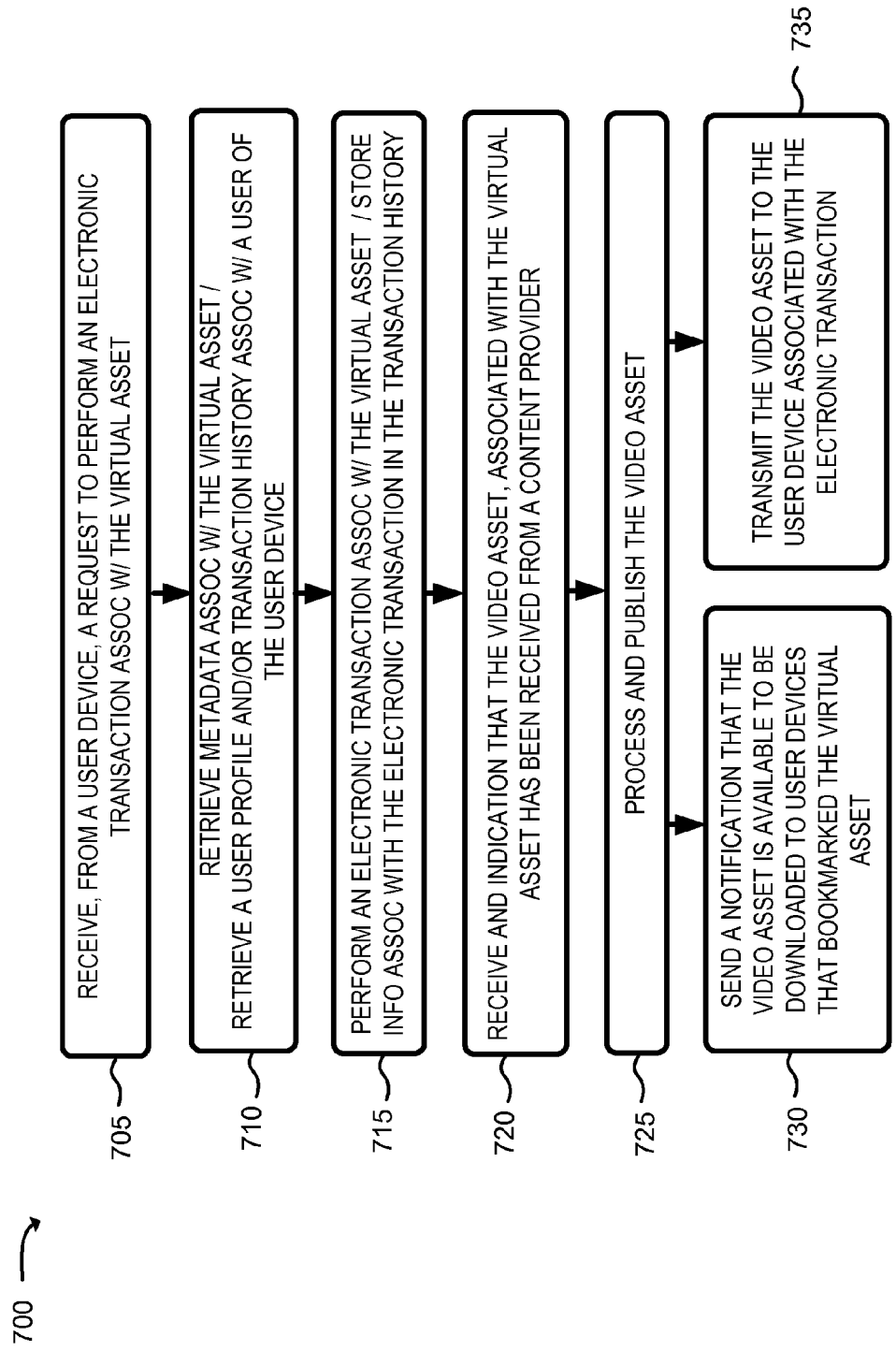
FIG. 7 is a flow chart of an example process for performing an electronic transaction, associated with a virtual video asset, according to an implementation described herein.

FIG. 7 is a flow chart of an example process 700 for performing an electronic transaction, associated with a virtual video asset, according to an implementation described herein. In an example implementation, process 700 may be performed by BOS 250. In another example implementation, some or all of process 700 may be performed by a device, or collection of devices separate from, or in combination with BOS 250.

As shown in FIG. 7, process 700 may include receiving, from a user device, a request to perform an electronic transaction associated with a virtual asset (block 705) and retrieving a profile and/or a transaction history that corresponds to a user of the user device, and/or retrieving metadata associated with the virtual asset (block 710). For example, user device 110 may select metadata, associated with a virtual asset, and may send a request, via a store front associated with VPS 120, to perform an electronic transaction (e.g., to purchase, rent, and/or subscribe to, etc.) associated with the virtual asset. BOS 250 may receive the request, via IMG server 220 when user device 110 is a set top box user device 110 and/or via application server 215 when user device is a different type of user device 110 than set top box user device 110. The different type of user device 110 may be a computer user device 110, a wireless handheld user device 110, a gaming user device 110, etc.

BOS 250 may, in response to the request, communicate with catalog server 235 (e.g., when the request is received via application server 215) and/or VOD server 230 (e.g., when the request is received via IMG server 220) to retrieve all or a portion of the metadata associated with the virtual asset. BOS 250 may also communicate with profile server 245 to retrieve a user profile associated with a user of user device 110. The user profile may include information associated with a type of user device 110 from which the selection was received. The user profile may also include information associated with another user device 110 associated with the user. BOS 250 may communicate with profile server 245 to retrieve a transaction history associated with a user of user device 110. The transaction history may include information associated with prior electronic transactions for video assets and/or virtual assets associated with user device 110 and/or the other user device 110. In another example implementation, BOS 250 may communicate with application server 215 to obtain a transaction history associated with user device 110 and/or the other user device 110 when user device 110 and/or the other user device 110 is a different type of user device 110 than a set top box-type of user device 110. BOS 250 may communicate with IMG server 220 to obtain another transaction history associated with user device 110 and/or the other user device 110 when user device 110 and/or the other user device 110 is a set stop box-type of user device 110.

As also shown in FIG. 7, process 700 may include performing an electronic transaction associated with the virtual asset and storing information, associated with the electronic transaction, in the transaction history (block 715). For example, based on a determination that the virtual asset has not been previously purchased, rented, or subscribed to by user device 110 or the other user device 110, BOS 250 may instruct billing server 255 to perform the electronic transaction, associated with the virtual asset, with user device 110. Based on a determination that the virtual asset has been previously purchased, rented, or subscribed to by user device 110 or the other user device 110, BOS 250 may not instruct billing server 255 to perform the electronic transaction.

Billing server 255 may receive an instruction, from BOS 250, to perform the electronic transaction and communicate with user device 110 to obtain payment information (e.g., credit card information, bank account information etc.) from user device 110, via a store front, and may process the payment information for a price that corresponds to the virtual asset. In another example, billing server 255 may store information associated with the virtual asset in an account associated with user device 110. The information associated with the virtual asset may include a price and/or identifier (e.g., a title) associated with the virtual asset, a time when the electronic transaction was performed, a date when the video asset, to which the virtual asset corresponds, will be available for distribution user device 110, etc. Billing server 255 may transmit an electronic receipt and/or confirmation to BOS 250 and/or to user device 110, via the store front, indicating that the electronic transaction is complete.

BOS 250 may receive the confirmation that the electronic transaction was complete and may store information associated with the electronic transaction in the transaction history. BOS 250 may also store information associated with the user device 110 and/or other user device 110 on a list associated with electronic transactions corresponding to the virtual asset. The list may identify user devices 110 that have performed electronic transactions associated with the virtual asset.

As further shown in FIG. 7, process 700 may include receiving an indication that the video asset, associated with the virtual asset, has been received and/or is available to be distributed (block 720) and processing and/or publishing the video asset (block 725). For example, BOS 250 may receive, at a future point in time after performing the electronic transaction, an indication that the video asset, to which the virtual asset corresponds, has been received by VCM server 240. BOS 250 may send, to VCM server 240, an instruction to process the video asset and/or to publish the processed video asset to VOD server 225 and/or CDN server 230. VCM server 240 may process the video asset by generating copies of the video asset in formats that can be distributed to user devices 110 and/or can be received, processed, and/or played by set top box-types of user devices 110 and types of user devices 110 that are different than set top box-types of user devices 110. VCM server 240 may publish the video asset by transmitting copies of the video asset to VOD server 240 that conform to a format that is supported by set top box user devices 110. VCM server 240 may publish the video asset by transmitting other copies of the video asset to CDN server 230 that conform to one or more other formats that are supported by the types of user devices 110 that are different than the set top box-type of user device 110.

In another example implementation, the video asset, to which the virtual asset corresponds, may have already been stored in VOD server 225 and/or CDN server 230 during a period of time before the video asset was available for distribution to user devices 110.

BOS 250 may transmit a notification to catalog server 235 and/or VOD server 235 that indicates that the video asset has been obtained and/or is available for distribution to user devices 110. The notification may indicate that metadata, associated with the virtual asset, is to be updated. Updating the metadata may include removing, from the metadata, information that indicates that the metadata corresponds to a virtual asset. Updating the metadata may also include storing, in the metadata, an indication that the video asset is stored in VOD server 225 and/or CDN server 230 and/or that the video asset is available to be downloaded.

As yet further shown in FIG. 7, process 700 may include sending a notification that the video asset is available for download to user devices that bookmarked the virtual asset (block 730). For example, BOS 250 may retrieve, from a memory associated with BOS 250, a list of user devices 110 that bookmarked the virtual asset. BOS 250 may transmit a notification that the video asset, associated with the virtual asset, is available to be downloaded to one or more user devices 110 identified on the list.

As still further shown in FIG. 7, process 700 may include transmitting the video asset to the user device associated with the electronic transaction (block 735). For example, BOS 250 may retrieve, from a memory associated with BOS 250, a list of user devices 110 with which an electronic transaction, associated with the virtual asset, was performed. BOS 250 may use the list of user devices 110 to identify user device 110, associated with the electronic transaction (e.g., as described in block 715 above). BOS 250 may retrieve, from profile server 245, a user profile associated with a user of user device 110. BOS 250 may identify a type of user device 110 that corresponds to user device 110 associated with the electronic transaction. BOS 250 may instruct VOD server 225 to transmit a copy of the video asset to user device 110 based on a determination that user device 110 is a set top box user device 110. BOS 250 may instruct CDN server 225 to transmit a copy of the video asset to user device 110 based on a determination that user device 110 is a type of user device 110 that is different than set top box user device 110. In another example implementation, BOS 250 may cause a copy of the video asset to be transmitted to another user device 110 that is identified in the user profile. BOS 250 may transmit, to profile server 245, an indication that the video asset was transmitted to user device 110 and/or the other user device 110.

Systems and/or methods, described herein, may enable a virtual asset to be created, managed, stored, and/or provisioned by a VPS. The systems and/or methods may enable different types of user devices, such as computer devices, wireless handheld devices, gaming devices, and/or set top boxes, to access and/or select the virtual asset via a store front associated with the video provisioning system. The systems and/or methods may permit the virtual asset to be sent to a user device, which allows a user, of the user device, to read a description of the virtual asset, view cover art associated with the virtual asset, read reviews associated with the virtual asset, etc. The systems and/or methods may send a notification, to the user device, that indicates that the video asset, to which the virtual asset corresponds, is not yet available and/or identifies a date when the video asset will be available. The systems and/or methods may allow the user device to bookmark the virtual asset, which may cause the VPS to notify the user device when the video asset becomes available for distribution. The systems and/or methods may allow the user device to purchase, rent, or subscribe to the virtual asset prior to the date of availability, which may cause the VPS to automatically transmit the video asset, to the user device, when the video asset becomes available.

The foregoing description provides illustration and description, but is not intended to be exhaustive or to limit the implementations to the precise form disclosed. Modifications and variations are possible in light of the above teachings or may be acquired from practice of the embodiments.

While series of blocks have been described with respect to FIGS. 5-7, the order of the blocks may be modified in other implementations. Further, non-dependent blocks may be performed in parallel.

It will be apparent that systems and/or methods, as described above, may be implemented in many different forms of software, firmware, and hardware in the implementations illustrated in the figures. The actual software code or specialized control hardware used to implement these systems and methods is not limiting of the embodiments. Thus, the operation and behavior of the systems and methods were described without reference to the specific software code—it being understood that software and control hardware can be designed to implement the systems and methods based on the description herein.

Further, certain portions, described above, may be implemented as a component that performs one or more functions. A component, as used herein, may include hardware, such as a processor, an ASIC, or a FPGA, or a combination of hardware and software (e.g., a processor executing software).

It should be emphasized that the terms "comprises"/ "comprising" when used in this specification are taken to specify the presence of stated features, integers, steps or components but does not preclude the presence or addition of one or more other features, integers, steps, components or groups thereof.

Even though particular combinations of features are recited in the claims and/or disclosed in the specification, these combinations are not intended to limit the disclosure of the embodiments. In fact, many of these features may be combined in ways not specifically recited in the claims and/or disclosed in the specification. Although each dependent claim listed below may directly depend on only one other claim, the disclosure of the embodiments includes each dependent claim in combination with every other claim in the claim set.

No element, act, or instruction used in the present application should be construed as critical or essential to the embodiments unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

What is claimed is:

1. A method performed by a server device and associated with a video provisioning system (VPS) comprising:
   receiving, by the server device, an indication that a video asset will become available for distribution, to a set top box and another user device, at a future time, wherein the other user device is a different type of user device than the set top box;
   retrieving, from a content provider, metadata associated with the video asset, wherein the metadata includes at least an identifier associated with the video asset; and
   storing, by the server device as a virtual asset, a portion of the metadata that includes the identifier, associated with the video asset, to a first store front associated with the VPS and a second store front associated with the VPS,
      wherein the first store front is an interactive media guide via which the set top box can access or obtain the virtual asset, and
      wherein the second store front is a website or a user interface via which the other user device can access or obtain the virtual asset.

2. The method of claim 1, where the metadata includes the identifier and one or more of:
   an image associated with the video asset,
   a description of the video asset,
   a review of the video asset,
   a date when the video asset becomes available for distribution,
   a price associated with the video asset, or
   a rating associated with the video asset.

3. The method of claim 1, where storing the portion of the metadata further includes:
   modifying the metadata in manner that associates the metadata with the virtual asset, where the modified metadata includes at least one of:
      the identifier that is modified to include an indication that the identifier is associated with the virtual asset, or
      a description of the video asset that is modified to include a notification that the video asset is not available for distribution until the future time.

4. The method of claim 1, further comprising:
   receiving, from a user device, a request for the virtual asset,
   retrieving, in response to the request, a user profile, associated with a user of the user device, where the user profile identifies whether the user device is the set top box or the other user device;
   transmitting the metadata to the user device, via the first store front, based on a determination that the user profile identifies the user device as the set top box; and
   transmitting the metadata to the user device, via the second store front, based on a determination that the user profile identifies the user device as the other user device.

5. The method of claim 1, further comprising:
   receiving, from a user device, a request to bookmark the virtual asset,
   retrieving, in response to the request, a user profile, associated with a user of the user device, where the user profile includes information associated with the set top box and the other user device;
   storing, in the user profile, the metadata as the bookmark; and
   storing the information associated with the set top box or the other user device in a list of user devices that have previously bookmarked the virtual asset.

6. The method of claim 5, further comprising:
   receiving, at the future time, an indication that the video asset is stored in the VPS,
   retrieving the list of user devices that have bookmarked the virtual asset, and
   transmitting, to the user devices, a notification that indicates that the video asset is available to be downloaded.

7. The method of claim 6, further comprising:
   modifying, in response to the indication that the video asset is stored in the VPS, the metadata in a manner that indicates that the video asset is available.

8. The method of claim 1, further comprising:
   receiving, from a user device, a request to perform an electronic transaction associated with the virtual asset,
   retrieving, in response to the request, a user profile associated with a user of the user device and a transaction history associated with the user, where the user profile includes information associated with the set top box and the other user device, and where the transaction history identifies a prior electronic transaction associated with the set top box or the other user device;
   determining that the virtual asset has not been previously purchased, rented, or subscribed to based on the transaction history;
   performing the electronic transaction, associated with the virtual asset, based on the determination that the virtual asset has not been previously purchased, rented, or subscribed to,
   storing the information associated with the electronic transaction in the transaction history; and
   storing the information, associated with the set top box or the other user device, in a list of user devices that have previously performed an electronic transaction associated with the virtual asset.

9. The method of claim 8, further comprising:
   receiving an indication that the video asset is stored in the VPS,
   retrieving the list of user devices that have previously performed the electronic transaction associated with the virtual asset, and
   sending an instruction that causes the video asset to be automatically transmitted to the set top box or the other user device at the future time.

10. A server device comprising:
a memory to store one or more virtual assets, the one or more virtual assets corresponding to one or more video assets that are not available for distribution, where each of the one or more virtual assets includes metadata associated with a respective different video asset of the one or more video assets; and
one or more processors to:
receive, from a user device among a plurality of different types of user devices associated with a user, a request for a virtual asset, wherein the request includes an identifier associated with one of the one or more video assets,
identify a video asset, of the one or more video assets, that corresponds to the identifier associated with the one of the one or more video assets,
retrieve, from the memory, metadata associated with the identified video asset,
process the retrieved metadata and provide the metadata as a virtual asset,
transmit the virtual asset to the user device in response to the request, and
provide access to the virtual asset to the plurality of different types of user devices associated with the user.

11. The server device of claim 10, where the one or more processors are further to:
receive, from the user device, a request to bookmark the virtual asset,
store, as the bookmark, all or a portion of the metadata in a user profile associated with the user device, and
store information, associated with the user device, in a list of user devices that have previously bookmarked the virtual asset.

12. The server device of claim 11, where the one or more processors are further to:
receive, at the future time, an indication that the video asset is available for distribution, and
transmit, to the user devices in the list of user devices, a notification that indicates that the video asset is available to be downloaded, based on the list of user devices that have previously bookmarked the virtual asset.

13. The server device of claim 10, where, before receiving the request for the virtual asset, the one or more processors are further to:
receive an indication that the video asset will become available for distribution to the user device at the future time,
retrieve, from a content provider, the metadata associated with the video asset; and
store, in the memory, the metadata associated with the video asset.

14. The server device of claim 13, where, when storing the metadata associated with the video asset, the one or more processors are further to:
store a portion of the metadata to a store front that allows the user device to browse, search for, or obtain the virtual asset, where the portion of the metadata corresponds to the identifier associated with the one of the one or more video assets.

15. The server device of claim 13, where the one or more processors are further to:
process the metadata to create the virtual asset, where the processed metadata includes at least one of:
a title, associated with the video asset, that has been modified to include an indication that the title is associated with the virtual asset,
a description of the video asset, that has been modified to include a notification that the video asset will be available for distribution at the future time, or
information associated with a status of the metadata, where the status indicates that the metadata is associated with the virtual asset.

16. The server device of claim 10, where the one or more processors are further to:
receive, from the user device, a request to purchase, rent, or subscribe to the virtual asset,
perform, in response to the request to purchase, rent, or subscribe to the virtual asset, an electronic transaction, associated with purchasing, renting, or subscribing to the virtual asset, that causes information, associated with the electronic transaction, to be stored in an account associated with a user of the user device, and
transmit, to the user device and as a result of the electronic transaction, a notification that the video asset will be automatically transmitted to the user device at the future time.

17. The server device of claim 16, where the one or more processors are further to:
retrieve a transaction history, associated with the user of the user device, to determine whether the virtual asset has been previously purchased, rented, or subscribed to by the user device, and
perform the electronic transaction based on a determination that the virtual asset has not been previously purchased, rented, or subscribed to by the user device.

18. A system comprising:
one or more communication devices; and
one or more devices comprising one or more processors to:
receive, from a content provider, metadata associated with a video asset, where the metadata includes information associated with the video asset and identifies a future time when the video asset will be available for distribution to a user device and at least another user device of a plurality of different types of user devices,
process the metadata to create a virtual asset, associated with the video asset, where the processed metadata includes at least an identifier associated with the video asset,
store the virtual asset to a store front that allows the user device and the at least another device to select the virtual asset to obtain the video asset,
transmit a notification or the video asset, to the user device and at the future time, based on the selection of the virtual asset by the user device, where the notification indicates that the video asset is available to be downloaded, and
provide access to the virtual asset to the user device and the at least another user device of the plurality of different types of user devices.

19. The system of claim 18, where the one or more processors of the one or more devices are further to:
receive, from the user device and via the store front, the selection of the virtual asset, and
transmit the processed metadata, as the virtual asset, to the user device as a result of receiving the selection of the virtual asset.

20. The system of claim 18, where the one or more processors of the one or more devices are further to:
receive, from the user device and via the store front, the selection of the virtual asset, where the selection of the virtual asset corresponds to a request to bookmark the virtual asset, and store the processed metadata, as the bookmark, in a user profile associated with a user, of the user device, in response to the request to bookmark the virtual asset, where storing the bookmark enables the user device to obtain the virtual asset within a period of time that is less than another period of time associated with obtaining the virtual asset via the store front.

21. The system of claim 20, where, when transmitting the notification or the video asset, the one or more processors are further to:

store information, associated with the user device, in a list of user devices, that have previously bookmarked the virtual asset, as a result of storing the processed metadata as the bookmark, and transmit the notification, to the user device and at the future time, based on the determination the information, associated with the user device, is stored in the list of user devices that have previously bookmarked the virtual asset.

22. The system of claim 18, where the one or more processors of the one more devices are further to:

receive, from the user device and via the store front, the selection of the virtual asset, where the selection of the virtual asset corresponds to a request to perform an electronic transaction associated with the virtual asset, obtain, from the processed metadata and in response to the request to perform the electronic transaction, a price associated with the virtual asset, perform the electronic transaction associated with the virtual asset based on the price associated with the virtual asset, and store information, associated with the user device, in a list of user devices that have previously performed an electronic transaction associated with the virtual asset.

23. The system of claim 22, where, when transmitting the notification or the video asset, the one or more processors are further to:

transmit the video asset, to the user device and at the future time, based on a determination that the information, associated with the user device, is stored in the list of user devices that have previously performed the electronic transaction associated with the virtual asset.

24. The system of claim 18, where the processed metadata includes at least one of:

a title, associated with the video asset, that has been modified to include an indication that a title is associated with the virtual asset, an image associated with the video asset, a description of the video asset, that has been modified to include an indication that the video asset will be available for distribution at the future time, or a price associated with the virtual asset.

* * * * *